US00PP14282P29

(12) United States Plant Patent
Watanabe et al.

(10) Patent No.: US PP14,282 P2
(45) Date of Patent: Nov. 11, 2003

(54) PETUNIA PLANT NAMED 'KIRIMAJI DOUBLE LAVENDER'

(50) Latin Name: *Petunia hybrida*
Varietal Denomination: Kirimaji Double Lavender

(75) Inventors: Saori Watanabe, Ujiie-machi (JP); Daigaku Takeshita, Utsunomiya (JP)

(73) Assignee: Kirin Brewery Company, Ltd., Tokyo (JP)

( * ) Notice: Subject to any disclaimer, the term of this patent is extended or adjusted under 35 U.S.C. 154(b) by 0 days.

(21) Appl. No.: 10/210,625

(22) Filed: Jul. 31, 2002

(51) Int. Cl.[7] ..... A01H 5/00
(52) U.S. Cl. ..... Plt./356
(58) Field of Search ..... Plt./356

*Primary Examiner*—Bruce R. Campell
*Assistant Examiner*—June Hwu
(74) *Attorney, Agent, or Firm*—C. A. Whealy

(57) ABSTRACT

A distinct cultivar of Petunia plant named 'Kirimaji Double Lavender', characterized by its low mounding cascading to prostrate plant habit; freely branching growth habit; early and freely flowering habit; violet purple-colored semi-double flowers; and good weather tolerance.

2 Drawing Sheets

Botanical classification/cultivar designation: Petunia hybrida cultivar Kirimaji Double Lavender.

BACKGROUND OF THE INVENTION

The present Invention relates to a new and distinct cultivar of Petunia plant, botanically known as Petunia hybrida, and hereinafter referred to by the name 'Kirimaji Double Lavender'.

The new Petunia is a product of a planned breeding program conducted by the Inventors in Tochigi, Japan. The objective of the breeding program is to create new double Petunia cultivars that have stronger growth and attractive flower coloration.

The new Petunia originated from a cross-pollination made by the Inventors in March, 1999, in Tochigi, Japan, of an unnamed proprietary selection of Petunia, not patented, as the female, or seed, parent with the Petunia cultivar Sonata Pure White, not patented, as the male, or pollen, parent. The new Petunia was discovered and selected by the Inventors as a single flowering plant within the progeny of the stated cross-pollination grown in a controlled environment in Tochigi, Japan, in July, 2000. The selection of this plant was based on its strong plant growth habit and attractive flower coloration.

Asexual reproduction of the new cultivar by terminal cuttings taken in a controlled environment in Tochigi, Japan, since July, 2000, has shown that the unique features of this new Petunia are stable and reproduced true to type in successive generations.

SUMMARY OF THE INVENTION

Plants of the cultivar Kirimaji Double Lavender have not been observed under all possible environmental conditions. The phenotype may vary somewhat with variations in environment such as temperature and light intensity without, however, any variance in genotype.

The following traits have been repeatedly observed and are determined to be the unique characteristics of 'Kirimaji Double Lavender'. These characteristics in combination distinguish 'Kirimaji Double Lavender' as a new and distinct cultivar of Petunia:

1. Low mounding cascading to prostrate plant habit.
2. Freely branching growth habit.
3. Early and freely flowering habit.
4. Purple violet-colored semi-double flowers.
5. Good weather tolerance; tolerant to wind, rain, and low and high temperatures.

Plants of the new Petunia can be compared to plants of the female parent, the unnamed proprietary Petunia selection. In side-by-side comparisons conducted by the Inventors in Tochigi, Japan, plants of the new Petunia differed from plants of the female parent primarily in flower form and color as plants of the female parent had single flowers that were white in color.

Plants of the new Petunia can be compared to plants of the male parent, the cultivar Sonata Pure White. In side-by-side comparisons conducted by the Inventors in Tochigi, Japan, plants of the new Petunia were not as upright and had slightly smaller flowers than plants of the cultivar Sonata Pure White. In addition, plants of the cultivar Sonata Pure White had white-colored flowers.

Plants of the new cultivar can be compared to plants of the cultivar Doubloon Pink, not patented. In side-by-side comparisons conducted by the Inventors in Tochigi, Japan, plants of the new Petunia differed from plants of the cultivar Doubloon Pink in the following characteristics:

1. Plants of the new Petunia had slightly smaller flowers than plants of the cultivar Doubloon Pink.
2. Flower color of plants of the new Petunia was violet purple whereas flower color of plants of the cultivar Doubloon Pink was dark pink.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photograph may differ slightly from the color values cited in the detailed botanical description which accurately describe the colors of the new Petunia.

The photograph on the first sheet comprises a side perspective view of a typical flowering plant of 'Kirimaji Double Lavender'.

The photograph on the second sheet comprises a close-up view of a typical flower of 'Kirimaji Double Lavender'.

DETAILED BOTANICAL DESCRIPTION

In the following description, color references are made to The Royal Horticultural Society Colour Chart except where general terms of ordinary dictionary significance are used. Plants used for the aforementioned photographs and the following description were grown in containers and under conditions which closely approximate commercial production conditions during the spring in Santa Paula, Calif. in a polyethylene-covered greenhouse. Plants used for the photographs and the description were about nine weeks from planting rooted young plants. During the production period, day temperatures ranged from 20 to 35° C., night temperatures ranged from 10 to 20° C., and light levels ranged from 20 to 40 klux.

Botanical classification: Petunia hybrida cultivar Kirimaji Double Lavender.

Parentage:

*Female, or seed, parent.*—Unnamed proprietary selection of Petunia hybrida, not patented.

*Male, or pollen, parent.*—Petunia hybrida cultivar Sonata Pure White, not patented.

Propagation:

*Type cutting.*—Terminal vegetative cuttings.

*Time to initiate roots.*—Summer: About 3 days at 25° C. Winter: About 5 days at 23° C.

*Time to produce a rooted young plant.*—Summer: About 21 days at 25° C. Winter: About 23 days at 25° C.

*Root description.*—Fine, fibrous, and white in color.

*Rooting habit.*—Freely branching; dense.

Plant description:

*Form.*—Annual flowering plant; low mounding cascading to prostrate plant habit; dense and bushy appearance.

*Plant height* (*from soil level to top of plant plane*).—About 12 cm.

*Plant diameter* (*area of spread*).—About 60 cm.

*Growth rate.*—Relatively rapid.

*Branching habit.*—Freely basal branching, about 25 lateral branches per plant; lateral branches develop at potentially every node; pinching is typically not required.

*Lateral branch description.*—Length: About 39 cm. Diameter: About 3 mm. Internode length: About 1.2 to 3 cm. Orientation: Initially upright, then horizontal. Texture: Pubescent; short, fine hairs. Strength: Strong, but flexible. Color: 144B.

*Foliage description.*—Leaves simple, generally symmetrical. Arrangement: Alternate before flowering, then opposite. Length: About 3.8 cm. Width: About 2.8 cm. Shape: Broadly elliptic to oval. Apex: Rounded. Base: Acute. Margin: Entire. Texture, upper and lower surfaces: Slightly pubescent; somewhat viscid. Venation pattern: Pinnate; arcuate. Color: Young foliage, upper surface: 146B. Young foliage, lower surface: 144A. Fully expanded foliage, upper surface: 146A. Fully expanded foliage, lower surface: 146B. Venation, upper surface: 144A. Venation, lower surface: 144B. Petiole length: About 1 cm. Petiole diameter: About 3 mm. Petiole color: 144B.

Flower description:

*Flower type and habit.*—Flowers face upright or outward; semi-double flower form; solitary and axillary; salverform. Freely flowering habit, about 15 to 16 flowers and flower buds per lateral stem. Flowers persistent.

*Fragrance.*—Slight; sweet, floral.

*Natural flowering season.*—Spring until frost in the autumn; flowering continuous during this period.

*Time to flower.*—Early flowering; plants begin flowering about two weeks after planting.

*Flower longevity on the plant.*—About 10 days.

*Flower size.*—Diameter: About 5.5 cm. Length (height): About 3.8 cm. Tube length: About 2.5 cm. Tube diameter, base: About 5 mm.

*Flower buds* (*showing color*).—Length: About 3 cm. Diameter: About 7 mm. Shape: Obovate. Color: 79D.

*Corolla.*—Arrangement/appearance: Outer whorl of about eight petals fused at base and surrounding inner whorl of about 12 to 14 petals. Petal length, outer and inner whorls of petals: About 2 cm. Petal width: Outer whorl of petals: About 2.2 cm. Inner whorl of petals: About 1.25 cm. Petal shape: Spatulate. Petal apex: Rounded, slightly pointed. Petal margin: Entire. Petal texture: Smooth, glabrous; velvety. Petal surface: Ruffled. Color: Petal, when opening, upper surface: 78A; venation, 64A. Petal, when opening, lower surface: 83C to 83D; venation, 144A. Petal, opened flower, upper surface: 81A; color becoming closer to 82B to 82C with subsequent development; venation, 64A. Petal, opened flower, lower surface: 84A to 84B; venation, 144A. Flower throat (inside): 155A; towards base, 144A; venation, 59A. Flower tube (outside): 156D; venation, 59C.

*Sepals.*—Arrangement/appearance: Single whorl of five sepals fused at base; star-shaped. Length: About 1 cm. Width: About 2 mm. Shape: Narrowly elliptic. Apex: Rounded. Margin: Entire. Texture, upper and lower surfaces: Slightly coarse; pubescent. Color: Upper surface: 146A. Lower surface: 146B.

*Peduncles.*—Length: About 2.8 cm. Width: About 1 mm. Strength: Strong. Angle: About 45° from stem. Texture: Pubescent. Color: 146A.

*Reproductive organs.*—Stamens: Quantity: About eight per flower. Anther shape: Oval. Anther size: About 2 mm by 2.5 mm. Anther color: 156B. Pollen amount: Very scarce. Pollen color: 188A. Pistils: Quantity: One per flower. Pistil length: About 1.8 cm. Stigma shape: Anvil-shaped. Stigma color: 146A. Style length: About 1.5 cm. Style color: 146C. Ovary color: 144A.

*Seed/fruit.*—Seed and fruit production has not been observed.

Disease/pest resistance: Plants of the new Petunia have not been noted to be resistant to pathogens and pests common to Petunia.

Weather/temperature tolerance: Plants of the new Petunia are tolerant to rain and wind and have been observed to tolerate temperatures from 3 to 35° C.

It is claimed:

1. A new and distinct cultivar of Petunia plant named 'Kirimaji Double Lavender', as illustrated and described.

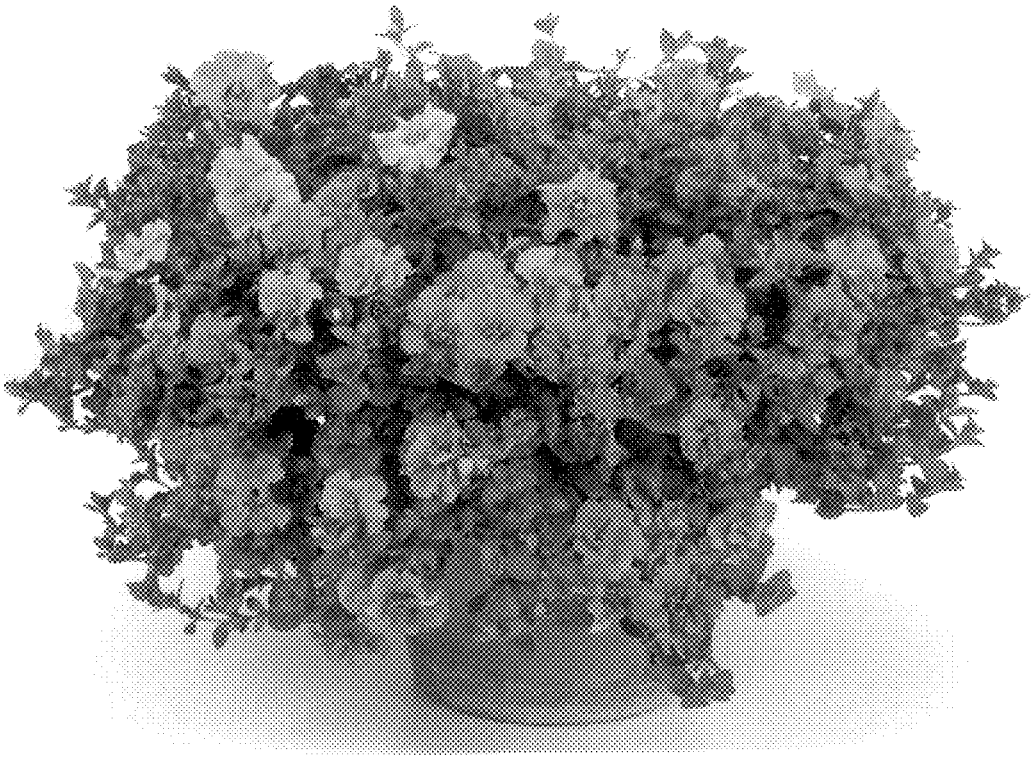

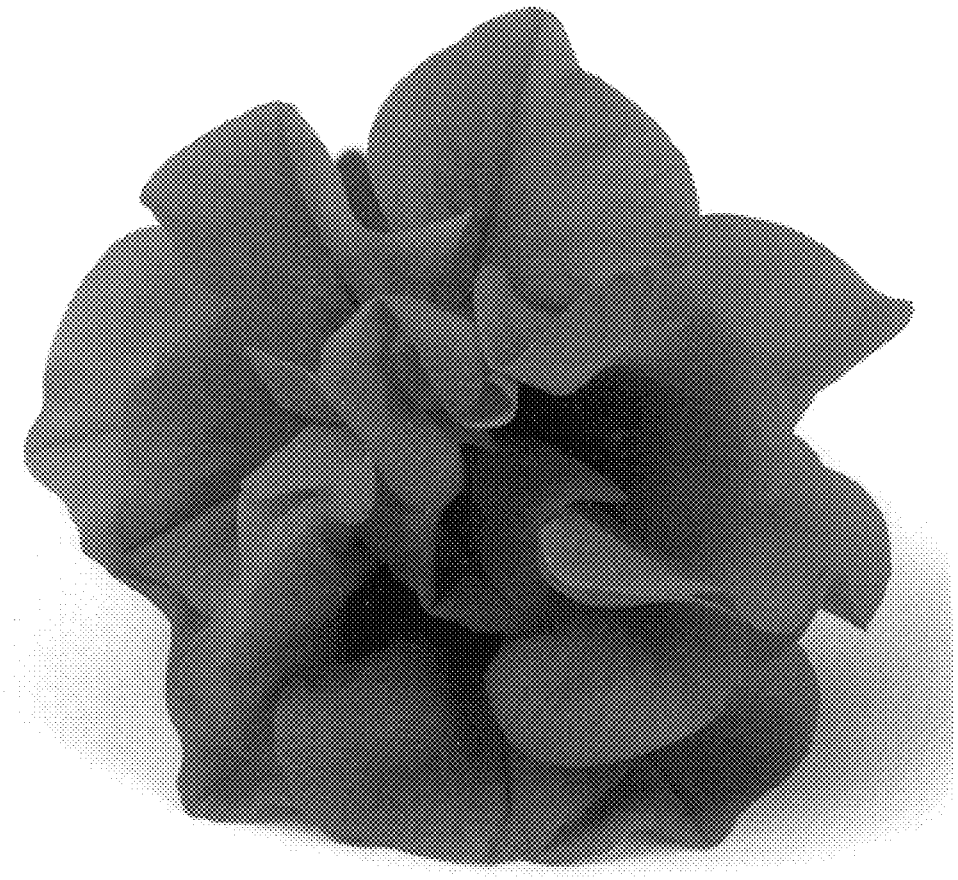

* * * * *